United States Patent [19]

Seely

[11] Patent Number: 4,656,255

[45] Date of Patent: Apr. 7, 1987

[54] PROTEIN RECOVERY

[75] Inventor: James E. Seely, Mundelein, Ill.

[73] Assignee: International Minerals & Chemical Corp., Terre Haute, Ind.

[21] Appl. No.: 773,671

[22] Filed: Sep. 9, 1985

[51] Int. Cl.[4] ............................ C07K 3/28; C07K 3/22
[52] U.S. Cl. ..................................... 530/412; 530/416; 530/417; 530/418; 530/422; 530/825; 435/68
[58] Field of Search ....................... 260/102 R; 435/68; 530/412, 416, 417, 418, 422, 825

[56] References Cited

U.S. PATENT DOCUMENTS 4,511,502  4/1985  Builder ............................ 260/112 R
4,511,503  4/1985  Olson ............................... 260/112 R
4,518,526  5/1985  Olson ............................... 260/112 R

*Primary Examiner*—John Kight
*Assistant Examiner*—Garnette D. Draper
*Attorney, Agent, or Firm*—W. R. Guffey; T. L. Farquer

[57] ABSTRACT

An improved process is described for recovering proteins from insoluble inclusion bodies produced in transformant microorganisms. Sidestream precipitates isolated from chromatography effluent are resolubilized in a denaturing agent and the resolubilized proteins are renatured either by direct dialysis into denaturant-free buffer or by dialysis into a weaker denaturing agent followed by dialysis into denaturant-free buffer.

20 Claims, No Drawings

PROTEIN RECOVERY

BACKGROUND OF THE INVENTION

This invention relates to methods for recovering, in a purified and biologically active form, proteins which are initially produced as insoluble, biologically inactive inclusion bodies in microorganisms that have been transformed with recombinant DNA expression vectors which direct expression of the proteins. More particularly, the invention relates to methods of recovering such proteins in improved yields by minimizing losses which occur during processing as a result of protein aggregation and precipitation.

Recombinant DNA technology allows the insertion of a vector carrying foreign ("heterologous") DNA into a microorganism in a manner which allows the heterologous DNA to be expressed; that is, the vector contains genetic instructions which direct the microorganism to produce a protein which is encoded by a portion of the heterologous DNA sequence. By growing transformant microorganisms in a fermentor and subjecting them to conditions under which the heterologous DNA is expressed, valuable proteins can be produced in large quantity at relatively low cost.

Unfortunately, many heterologous proteins which are produced in transformant microorganisms do not fold into their native three-dimensional conformation in the host cell environment. Improper folding of the expressed protein has several untoward consequences. In the first place, the improperly folded proteins tend to form aggregates which are insoluble within the host cell. These insoluble aggregates are recognizable within the cell as "inclusion bodies", sometimes also referred to as "refractile bodies." The formation of inclusion bodies may also be partially caused by oligomerization of the protein through the formation of intermolecular disulfide bonds. Not only are the improperly folded proteins insoluble, but also they are biologically inactive. As exemplary of heterologous proteins which form insoluble, biologically inactive inclusion bodies upon expression in a host cell, one can mention animal growth hormones such as bovine growth hormone and porcine growth hormone.

In order to produce useful proteins, it is necessary to convert the improperly folded inclusion body proteins into their native conformations, in which they are soluble and biologically active. Moreover, it is necessary to purify the proteins in order to remove contaminating cell debris and host cell proteins. A number of schemes have been proposed for converting inclusion body proteins into their soluble, native conformations and for purifying the proteins to produce commercially acceptable products. All of the proposed schemes are characterized by an initial unfolding or denaturing step in which the inclusion body proteins are treated with a strong denaturing agent (sometimes referred to as a chaotrope) in order to unfold the protein molecules and render them soluble. Guanidine hydrochloride is the most commonly employed strong denaturant for this purpose. At a subsequent stage in the recovery process, the denaturing agent is removed so that the unfolded protein molecules can refold into their native conformation, a process also referred to herein as "renaturation".

U.S. Pat. No. 4,511,503 discloses a typical recovery scheme of the type just described. A number of variations on this scheme, including additional processing steps directed to purification and/or yield enhancement, have been proposed. Thus, for example, U.S. Pat. No. 4,511,502 discloses a process wherein the solubilized protein/denaturant solution is passed over a molecular sieve or centrifuged at high speed to remove higher molecular weight components. U.S. Pat. No. 4,518,526 discloses a process in which a transformant cell culture is treated with a buffered solution having sufficient ionic strength to solubilize most of the host cell protein while the heterologous protein remains insoluble. The cells are then lysed, the supernatant containing the solubilized host cell protein removed and the insoluble inclusion bodies solubilized in the strong denaturant.

Other publications disclosing denaturation/renaturation schemes for converting inclusion body proteins into their soluble, native conformations include PCT publication No. WO 83/04418, European Patent Application Publication No. 0 123 928, European Patent Application Publication No. 0 121 775, European Patent Application Publication No. 0 116 778 and European Patent Application Publication No. 0 114 507.

At some point in the recovery process, it is necessary to subject the solubilized protein to a purification step in order to remove contaminants such as unwanted host cell proteins. Conventional techniques of protein purification including ion-exchange chromatography, affinity chromatography and the like are generally employed for this purpose. The purification step is performed, in some cases, prior to removal of the denaturing agent and, in other cases, subsequent to the removal of the denaturing agent. Theoretically, the denaturation/renaturation schemes discussed above provide a facile solution to the problem of recovering inclusion body proteins in soluble, biologically active form free of contaminants. The practical implementation of these schemes, however, has been plagued by problems of low yield and uneconomical operation. These problems result largely from the tendency of the solubilized protein to reaggregate, either because the proteins refold improperly upon removal of the denaturant or because the conditions under which purification is carried out interfere with the ability to maintain the protein in a soluble form. We have found that the use of guanidine solubilization followed by removal of the guanidine to refold the protein and purification on an ion-exchange chromatography column results in product recoveries from about 4% to about 12%, based on the amount of desired protein which is present in the inclusion bodies. These yields are far below those which are considered minimally acceptable from a commercial standpoint.

SUMMARY OF THE INVENTION

This invention provides a method for recovering purified, soluble, biologically active proteins from insoluble inclusion bodies in substantially improved yields. In the method of the invention, sidestream precipitates comprised of reaggregated protein are recovered from the main process stream following chromatographic purification. They are then resolubilized and returned to the main process stream under conditions in which the solution of recovered sidestream protein is compatible with the protein solution in the main process stream.

In one embodiment of the invention, insoluble protein aggregates are isolated from a purification column effluent containing both soluble, purified protein and insoluble protein aggregates; the isolated protein aggregates are solubilized in a denaturing agent; the solution is dialyzed against a solution containing a weaker denaturing agent to partially renature the protein; the solution of partially renatured protein is dialyzed against a denaturant-free buffer solution to remove the denaturant and to complete renaturation of the protein; and the renatured protein solution is admixed with the soluble, purified protein obtained from the purification column.

In another embodiment of the invention, protein aggregates are isolated from a purification column effluent containing both soluble, purified protein and insoluble protein aggregates; the isolated protein aggregates are solubilized in a denaturing agent; the solution is dialyzed directly against a denaturant-free buffer solution to obtain a solution containing both soluble protein and insoluble protein aggregates; the insoluble protein aggregates are removed from the solution; and the solution containing the soluble protein is admixed with the soluble protein solution obtained from the purification column.

The former embodiment of the invention, involving a two-step dialysis of the renatured protein aggregates, gives as much as 75% recovery of soluble protein, although some of the soluble protein is in the form of multimeric material. The latter embodiment of the invention, involving a single-step dialysis of renatured protein aggregates, gives a substantially lower recovery of soluble protein, but almost all of the soluble protein obtained is in the form of monomeric material. In either case, the introduction of the recovered side stream aggregates into the main process stream of the purification and recovery process results in a substantial increase in the overall recovery of soluble, biologically active protein.

DETAILED DESCRIPTION OF THE PREFERRED EMBODIMENTS

As previously indicated, this invention provides a method for improving the overall yield of soluble, biologically active protein which is obtainable in a purification and activation process for the recovery of proteins produced as insoluble, biologically inactive inclusion bodies in transformant microorganisms. The method of the invention can be used to recover any protein which is produced in the form of insoluble, biologically inactive inclusion bodies in transformant microorganisms, i.e., microorganisms which have been transformed with recombinant DNA vectors that direct the expression of genes coding for heterologous proteins. In specific embodiments of the invention, the proteins which are recovered in high yield are animal growth hormones such as bovine growth hormone (bGH) or porcine growth hormone (pGH).

It is to be understood that reference herein to proteins generally—e.g., hormones and enzymes—or to specific proteins such as bGH and pGH is not intended to be restricted to molecular species having the full amino acid sequence of the natural protein. Rather, it is also intended to include fragments of the protein having various portions of the sequence deleted and to include proteins or fragments thereof having various substitutions or modifications in their natural sequences which do not destroy the biological activity of the molecules.

The genes for bGH and pGH have been cloned onto expression vectors and used to transform $E.$ $coli$ host cells. European Patent Application Publication No. 0 103 395 describes the construction of a transformant strain of $E.$ $coli$ containing a first plasmid which codes for $\Delta 9(Ser)bGH$ (bGH less its 9 N-terminal amino acids and having an additional serine residue at the N-terminus) under the control of the $\lambda P_L$ promoter-operator and which has a Shine-Dalgarno region derived from bacteriophage mu. The transformant also contains a second plasmid, pcI857, which codes for the production of the cI857 temperature-sensitive repressor protein. The repressor protein can be inactivated by raising the temperature to about 42° C., thereby inducing expression of $\Delta 9(Ser)bGH$. A transformant strain of this type, $E.$ $coli$ HB101 ($P_L$-mu-$\Delta 9(Ser)bGH$ and pcI857) has been deposited, with the designation $E.$ $coli,$ IMC No. 1, at The American Type Culture Collection, Rockville, Md. with accession No. 53030.

Construction of a similar transformant strain which codes for the production of $\Delta 7pGH$ (porcine growth hormone less its first 7 N-terminal amino acids) is described in European Patent Application Publication No. 0 104 920. A transformant strain of this type, $E.$ $coli$ HB101 ($P_L$-mu-$\Delta 7pGH$ and pcI857) has been deposited, with the designation $E.$ $coli,$ IMC No. 2, at The American Type Culture Collection, Rockville, Md., with accession No. 53031.

$E.$ $coli,$ IMC No. 1 and $E.$ $coli,$ IMC No. 2 are prolific producers of $\Delta 9(Ser)bGH$ and $\Delta 7pGH$, respectively. In both instances, the expressed protein is sequestered within the cell in the form of insoluble, biologically inactive inclusion bodies which are visible under a microscope.

Preferred embodiments of the recovery method of the invention can be better understood with reference to Scheme I and Scheme II below. Referring to Scheme I, the transformant cells, which have been grown in a fermentor and which have accumulated protein in the form of inclusion bodies, are lysed, either mechanically, chemically or enzymatically, to allow isolation of the inclusion bodies which are sequestered within the cells. The inclusion bodies can be separated from the bulk of the remainder of cellular material by centrifugation and washing in a buffer to produce a wet inclusion body paste.

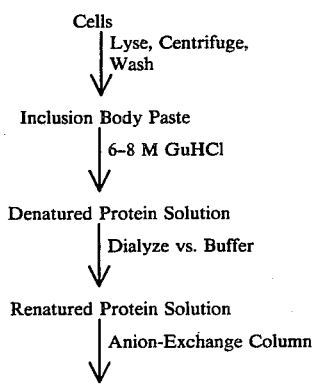

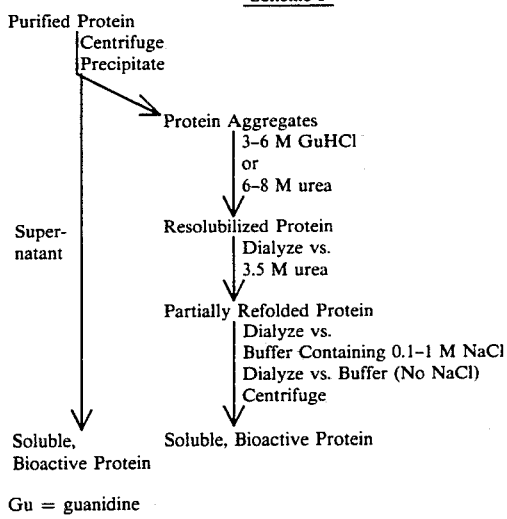

Gu = guanidine

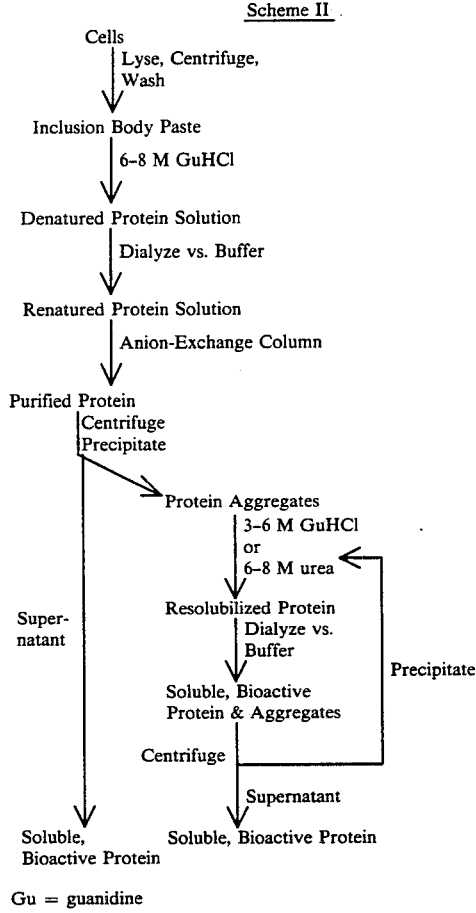

Gu = guanidine

The inclusion body proteins in the wet inclusion body paste are solubilized by extraction into a buffered solution containing a strong denaturing agent. As used herein, the term "strong denaturing agent" refers to guanidine or urea denaturing agents which are capable of completely but reversibly denaturing the inclusion body proteins at concentrations from about 6 M to about 8 M. Preferred denaturing agents for this purpose include guanidine salts, particularly guanidine hydro-chloride. If desired, detergents such as sodium dodecyl sulfate (SDS) or Triton X 100 at concentrations of about 1% can be employed as strong denaturing agents. As disclosed in U.K. Patent Application No. GB 2 138 004, aqueous alkaline solutions having pHs in the range from pH 9.0 to pH 11.5 can also be used as strong denaturing agents. Extraction of the inclusion body proteins into the strong denaturant causes the protein molecules to unfold and become soluble. At this point, the solution is clarified, for example, by centrifugation, to remove any suspended insoluble material.

The denaturing agent is then removed, for example by dialyzing the solution against multiple volumes of denaturant-free buffer, in order to renature the protein. The buffered solution containing the renatured protein can be centrifuged in order to remove any reaggregated material which may have formed during the renaturation process. The renatured inclusion body proteins are then purified chromatographically.

Any conventional means of chromatographic purification of the protein may be employed. For example, the protein may be purified by affinity chromatography, size exclusion chromatography, ion-exchange chromatography or any other known and conventionally employed chromatographic technique. These techniques may be used singly or in sequence. As illustrated in Scheme I and Scheme II, a preferred method of purifying the solubilized protein is anion-exchange chromatography. Preferred anion-exchange columns include QAE-Sephadex A25, DEAE Sepharose CL-6B, DE-53 cellulose, DE-52 cellulose, DE-51 cellulose, Cellufine AM, Indion DEAE, Indion QAE or Zetaprep QAE. Purification by anion-exchange chromatography is carried out in a conventional manner. Upon elution from the purification column, a substantial amount of reaggregation of protein normally will have occurred. Thus, the effluent from the column comprises a cloudy solution containing both soluble and insoluble protein. The column can be washed with a buffer solution in order to remove any entrained protein aggregates which remain in the column.

Again referring to Scheme I, the insoluble, reaggregated protein is isolated from the purification column effluent, preferably by centrifugation. The precipitate comprising the reaggregated protein (sidestream protein) is then resolubilized.

We have found that, once the protein has been purified, solubilization of reaggregated protein can be achieved using somewhat weaker denaturing agents or using strong denaturing agents at lower concentrations than are required for the initial solubilization of proteins from the wet inclusion body paste. Whereas 6 to 8 M guanidine hydrochloride is normally required to solubilize the inclusion bodies (urea solutions are generally not capable of solubilizing the inclusion bodies), the aggregated and purified proteins obtained from the purification column effluent can be satisfactorily solubilized in a solution of 3–6 M guanidine hydrochloride or 6–8 M urea. Since guanidine hydrochloride is an expensive reagent, the ability to use a relatively weak denaturant to resolubilize sidestream aggregates from the purification column effluent makes the recovery process economically efficient. Additionally, the use of relatively weak denaturants to solubilize the proteins may reduce the risk of reaggregation upon removal of the denaturant, thereby enhancing yield.

A preferred denaturant for use in resolubilizing the sidestream protein is 3-6 M guanidine-HCl. Typically, the insoluble sidestream proteins are dissolved in 3 M guanidine-HCl at 40 vol./gram of protein. Dissolution is generally complete within 2-3 hours. If desired, a reducing agent such as 5 mm glutathione may be added to inhibit the formation of intermolecular disulfide bonds; however I have found that this is generally unnecessary since very little intermolecular disulfide bonding occurs.

In accordance with the embodiment of the invention illustrated in Scheme I, the denatured protein aggregates from the purification column effluent are renatured in a stepwise process. In the first step, the solution of denatured proteins is dialyzed against multiple volumes of a buffered solution containing a relatively dilute denaturing agent in order to allow the protein to partially refold. Typically, the dilute denaturing agent solution is 3-6 M urea, preferably about 3.5 M urea. The solution containing the partially refolded protein and the dilute denaturing agent is then dialyzed against denaturant-free buffer in order to remove the weaker denaturing agent and allow the protein to refold into its native conformation.

Preferably, the solution containing partially renatured protein is dialyzed first against a denaturant-free buffer solution containing from about 0.1 to 1.0 M NaCl, followed by a second dialysis against NaCl-free buffer. The intermediate dialysis into NaCl-containing buffer causes selective precipitation of soluble protein aggregates, which are not biologically active, while allowing a significant portion of biologically active monomeric protein to refold.

We have found that reaggregation during the recovery of sidestream proteins can be inhibited by controlling the pH and temperature of the buffer solutions used in the process. Preferably the buffer solutions have pH's in the range from about pH 9.0 to about pH 10.0 and the temperature of the solutions is maintained at about 4° C. to about 10° C. Preferred buffers for use in this range are ethanolamine HCl, glycine NaOH and Cornell buffer (carbonate-bicarbonate buffer).

In order to allow reintroduction of the recovered sidestream proteins into the main process stream, it is essential that the final buffer solution into which the recovered side stream proteins are dialyzed is compatible with, and preferably the same as, the buffer solution which is employed in the main process stream at the point of reintroduction. By matching the final buffer solution of the recovered sidestream proteins to the chromatography column eluate buffer, the two streams can be admixed at this point in order to obtain an increased yield of soluble, biologically active protein.

Referring to Scheme II, it can be seen that the essential difference between the illustrated embodiment and the embodiment of Scheme I lies in the method by which the resolubilized sidestream proteins are renatured. In the embodiment illustrated in Scheme II, the resolubilized protein aggregates are renatured by dialysis directly against denaturant-free buffer solution, i.e., without the use of an intermediate stage dilute denaturant. While this procedure results in reaggregation of some protein during the renaturing process, we have found that the protein which remains in solution is essentially all monomeric. Consequently, the soluble protein which is recovered from the sidestream in this embodiment may have a somewhat higher level of biological activity per gram of protein than that recovered in the embodiment represented in Scheme I. Following dialysis against the denaturant-free buffer, the resulting solution is centrifuged and the supernatant containing the soluble, biologically active protein is reintroduced into the soluble, renatured protein in the main process stream. The reaggregated protein in the precipitate can be recycled as shown.

The following examples are intended to illustrate further the practice of the invention and are not intended to limit the scope of the invention in any way.

EXAMPLE I

An *E. coli* host strain, MC1061, transformed with the plasmid coding for Δ9(Ser)bGH and the plasmid pcI857 (ATCC 53030) was cultured under Δ9(Ser)bGH-producing conditions. The cells were lysed and the Δ9(Ser)bGH-containing inclusion bodies were precipitated by centrifugation. Following a wash procedure to remove contaminants, the inclusions were solubilized in (40 volumes) 50 mM glycine NaOH (pH 9.8) containing 8 M guanidine HCl and 5 mM reduced glutathione. The solubilized inclusions were then dialyzed vs. 50 mM glycine NaOH, pH 9.8 containing 3.5 M urea, 10% sucrose, 1.0 mM reduced glutathione and 0.1 mM oxidized glutathione (to partially refold the protein) followed by dialysis against 60 mM ethanolamine HCl, pH 9.8 containing 10% sucrose (to completely refold the protein). Precipitated protein was removed by centrifugation and the pH of the supernatant was adjusted to 9.0. The sample was then loaded onto a Whatman DE-52 cellulose column (maximal loading 7 g protein/1 resin) that had been equilibrated with 60 mM ethanolamine, pH 9.0 containing 5% sucrose. Growth hormone-containing fractions (which eluted in the breakthrough fractions of the column) were adjusted to pH 9.8 and concentrated approximately tenfold using an Amicon DC-50 UF ultrafiltration apparatus. The concentrated growth hormone sample was then centrifuged, the supernatant saved for downstream finishing steps, and the precipitates saved for recycling.

The precipitated material was dissolved in 40 volumes (ml/g) 3 M guanidine HCl in 50 mM glycine NaOH buffer (pH 9.8) containing 5 mM reduced glutathione. Solubilization time was 4 hours at 25° C. (All previous steps to this point and all subsequent steps were done at 4°-10° C.) The solubilized precipitates were dialyzed against 10 volumes 3.5 M urea in 50 mM glycine NaOH (pH 9.8) containing 5% sucrose, 5.0 mM reduced glutathione followed by dialysis against 10 vol. 60 mM ethanolanine buffer (pH 9.8) containing 5% sucrose and 1 M NaCl. Final dialysis was against this same ethanolamine buffer without NaCl. This sample was then centrifuged at 10,000 xg for 10 minutes and the resulting supernatant analyzed for soluble protein using the method of Bradford (*Anal. Biochem.*, 72:248-254 [1976]). The material was also analyzed by SDS-PAGE and YM-100 membrane ultrafiltration (as a test for presence of high molecular weight contaminants). The material was tested for proper folding/tertiary structure by the rat liver receptor binding assay as described by J. Roth (*Methods of Enzymology*, 37:66-81 [1975]).

Nearly a 60% recovery of soluble material was obtained from the solubilized DE-52 precipitate. Approximately 75% of the material permeated a YM-100 (100,000 molecular weight cut-off) ultrafiltration membrane, indicating only a small amount of high molecular weight material in the sample. (This method usually gives an underestimate of the actual amount of monomeric growth hormone.)

SDS-PAGE results also showed few high molecular weight contaminants in the preparation. The receptor binding activity of the sample was slightly reduced on a per weight basis (having approximately 53% the activity of a standard, natural bGH); however, this may have been due to the small amount of contaminants in the preparation.

EXAMPLE II

Δ9(Ser)bGH was produced and processed in the same manner described in Example I up to and including the purification on the DE-52 column. The post DE-52 column bGH precipitates were isolated and dissolved in (40 vol.) 3 M guanidine HCl, in 50 mM glycine NaOH buffer (pH 9.8) containing 5 mM reduced glutathione. The samples were dialyzed against 3.5 M urea in 50 mM glycine NaOH (pH 9.8) containing 5% sucrose. Following this dialysis, samples were dialyzed against 60 mM ethanolamine buffer, pH 9.8, containing 5% sucrose and no NaCl. After this dialysis the material was centrifuged at 10,000 xg for 10 minutes and the supernatant analyzed as in Example I. (All steps except 3 M guanidine dissolution step were done at 4°–10° C.)

Although essentially all of this material remained soluble following the refolding out of 3 M guanidine, SDS-PAGE and YM-100 ultrafiltration revealed that this material contained a considerable amount of high molecular weight aggregates. Receptor binding activity of this material (on a per weight basis) was 25% that of a control standard bGH, which probably reflects the relatively low activity of the high molecular weight contaminants. Even though this material was too aggregated to be reintroduced into the process stream from which it came (post DE-52 concentration-centrifugation step), it can be reintroduced further upstream in the process at the DE-52 chromatography step.

EXAMPLE III

9(Ser)bGH was prepared and processed as described in Examples I and II up to and including the DE-52 column and the precipitates from the DE-52 column again dissolved in 3 M guanidine HCl, 50 mM glycine-NaOH (pH 9.8) containing 5 mM reduced glutathione (at 25° C). The solubilized precipitates were dialyzed against 2×20 volumes of 60 mM ethanolamine HCl, pH 9.8 containing 5% sucrose at 5° C. The refolded samples were centrifuged at 10,000 xg for 10 minutes and analyzed as in Examples I and II.

Although a relatively low recovery of soluble protein was obtained by this method (15% of the 3 M guanidine solubilized material remained in solution), this material was entirely monomeric 9(Ser)bGH as judged by SDS-PAGE and YM-100 ultrafiltration (over 90% permeable by ultrafiltration, which is as good as that obtained with a natural bGH standard). This material was also 85% active in the rat liver membrane receptor binding assay and could have been directly reintroduced into the process stream fromm whence it came (post DE-52 concentration/centrifugation supernatant).

What is claimed is:

1. In a process for recovering pure, biologically active protein from inclusion bodies produced in transformant microorganisms, wherein inclusion body proteins are solubilized in a denaturing agent, renatured by removal of the denaturing agent and purified by column chromatography, the improvements comprising:
    (a) isolating insoluble protein aggregates from the chromatography column effluent;
    (b) resolubilizing the isolated protein aggregates in a buffer solution containing a denaturing agent;
    (c) dialyzing the solution of resolubilized protein aggregates against a buffer solution containing a weaker denaturing agent to partially renature the protein; and
    (d) dialyzing the solution of partially renatured protein against a denaturant-free buffer solution to produce a solution of biologically active protein.

2. An improved process as claimed in claim 1, wherein the solution of partially renatured protein is dialyzed first against a denaturant-free buffer solution containing from about 0.1 to 1.0 M NaCl and then against a denaturant-free buffer solution containing no NaCl.

3. An improved process as claimed in claim 1, which further comprises combining the solution obtained in step (d) with the solution of biologically active protein obtained as the chromatography column effluent.

4. An improved process as claimed in claim 1, wherein the protein aggregates isolated from the chromatography column effluent are resolubilized in a buffered solution of a denaturant selected from 3–6 M guanidine hydrochloride and 6–8 M urea.

5. An improved process as claimed in claim 1, wherein the buffer solution of weaker denaturant is a urea solution having a concentration of about 3.5 M.

6. An improved process as claimed in claim 1, wherein the protein is an animal growth hormone.

7. An improved process as claimed in claim 1, wherein the protein is selected from bovine growth hormone and porcine growth hormone.

8. An improved process as claimed in claim 1, wherein the denaturation and renaturation in steps (b), (c) and (d) are carried out in buffered solution having pH's from about pH 9 to about pH 10.

9. An improved process as claimed in claim 8, wherein the denaturation and renaturation solutions of steps (b), (c) and (d) are maintained at a temperature from about 4° C. to about 10° C.

10. An improved process as claimed in claim 1, wherein the chromatography column is an anion-exchange column.

11. In a process for recovering pure, biologically active protein from inclusion bodies produced in transformant microorganisms, wherein inclusion body proteins are solubilized in a denaturing agent, renatured by removal of the denaturant and purified by column chromatography, the improvements comprising:
    (a) isolating insoluble protein aggregates from the chromatography column effluent;
    (b) resolubilizing the isolated protein aggregates in a buffer solution containing a weak denaturing agent;
    (c) dialyzing the solution of resolubilized protein aggregates against a denaturant-free buffer solution to produce a solution containing biologically active protein; and
    (d) removing reaggregated protein from the solution.

12. An improved process as claimed in claim 11, which further comprises combining the solution obtained in step (d) with the solution of biologically active protein obtained as the chromatography column effluent.

13. An improved process as claimed in claim 11, wherein the protein aggregates isolated from the chromatography column effluent are resolubilized in a buffered solution of a denaturant selected from 3-6 M guanidine hydrochloride and 6-8 M urea.

14. An improved process as claimed in claim 11, wherein the protein is an animal growth hormone.

15. An improved process as claimed in claim 11, wherein the protein is selected from bovine growth hormone and porcine growth hormone.

16. An improved process as claimed in claim 11, wherein the denaturation and renaturation solutions in steps (b) and (c) have pH's from about pH 9 to about pH 10.

17. An improved process as claimed in claim 11, wherein the denaturation and renaturation solutions of steps (b) and (c) are maintained at a temperature from about 4° C. to about 10° C.

18. An improved process as claimed in claim 11, wherein the chromatography column is an anion-exchange column.

19. An improved process as claimed in claim 11, wherein the buffer solution of weaker denaturant is a urea solution having a concentration of about 3.5 M.

20. And a process for recovering a pure, biologically active porcine or bovine growth hormone from inclusion bodies produced in transformant microorganisms, wherein inclusion body proteins are solubilized in a denaturing agent, renatured by removal of the denaturant and purified by column chromatography, the improvements comprising:

(a) isolating insoluble protein aggregates from the chromatography column effluent;

(b) resolubilizing the isolated protein aggregates in a buffer solution containing a weak denaturing agent selected from 3-6 M guanidine hydrochloride and 6-8 M urea, said buffer solution having a pH from about pH 9 to about pH 10, said buffered solution maintained at a temperature from about 4° C. to about 10° C.;

(c) dialyzing the solution of resolubilized protein aggregates against a denaturant-free buffer solution to produce a solution containing biologically active porcine or bovine growth hormone, said buffer solution having a pH from about pH 9 to about pH 10, said buffered solution maintained at a temperature from about 4° C. to about 10° C.; and (d) removing reaggregated protein from the solution.

* * * * *